United States Patent [19]

Kleinman et al.

[11] Patent Number: 5,158,874
[45] Date of Patent: Oct. 27, 1992

[54] DETERMINING METASTIC POTENTIAL OF TUMOR CELLS AND ISOLATING METASTIC TUMOR CELLS

[75] Inventors: Hynda K. Kleinman; George R. Martin, both of Bethesda, Md.

[73] Assignee: The United States of America as represented by the Department of Health and Human Services, Washington, D.C.

[21] Appl. No.: 291,623

[22] Filed: Dec. 29, 1988

Related U.S. Application Data

[60] Division of Ser. No. 867,027, May 27, 1986, Pat. No. 4,829,000, which is a continuation-in-part of Ser. No. 771,409, Aug. 30, 1985, abandoned.

[51] Int. Cl.$^5$ .......................... C12Q 1/04; C12N 5/00
[52] U.S. Cl. ........................................ 435/34; 435/29; 435/240.2; 435/240.23; 435/240.243; 435/948
[58] Field of Search ................ 435/34, 240, 241, 948, 435/273, 267, 240.23, 240.243, 240.2

[56] References Cited

PUBLICATIONS

Terranova Science 226:982–984 (1984).
Martin (1984) Ciba Found. Symp. 108, 197–212.
Kleinman et al, Basement Membrane Complexes with Biological Activity, Biochemistry 25:312–318 (1986).
Albini et al, a Rapid In Vitro Assay for Quantitating the Invasive Potential of Tumor Cells, Cancer Research 47:3239–3245 (1987).
Kleinman et al., Formation of a Supramolecular Complex Is Involved in the Reconstitution of Basement Membrane Components, Biochemistry, 22:4969–4974 (1983).
Hendrix et al, Comparison of Tumor Cell Invasion Assays: Human Amnion versus Reconstituted Basement Membrane Barriers, Invasion and Metastasis 9:278–297 (1989).
Starkey, Cell–Matrix Interactions During Tumor Invasion, Cancer and Metastasis Reviews 9:113–123 (1990).
Terranova et al, Use of a Reconstituted Basement Membrane to Measure Cell Invasiveness and Select for Highly Invasive Tumor Cells, Proc. Natl. Acad. Sci. USA 83:465–469 (1986).

Primary Examiner—David M. Naff
Assistant Examiner—Jane A. Williams
Attorney, Agent, or Firm—Cushman, Darby & Cushman

[57] ABSTRACT

The present invention discloses a biologically active basement membrane composition. When polymerized under physiogical conditions, the composition forms gel-like structures whose ultrastructure resembles interconnected thin sheets of the lamina densa zone of basement membrane. The major components of the composition include laminin, type IV collagen, heparan sulfate proteoglycan, entactin and nidogen. These components polymerize in constant proportions when redissolved and allowed to reconstitute. Molecular sieve studies on the soluble extract demonstrate that laminin, entactin and nidogen are associated in a large but dissociable complex. The reconstituted matrix is biologically active and stimulates the growth and differentiation of a variety of cells, including epithelial cells, nerve cells, hair follicles and the like. The reconstituted matrix can also be used for determining metastatic potential of tumor cells and for isolating metastatic tumor cells.

4 Claims, 8 Drawing Sheets

FIG. IA
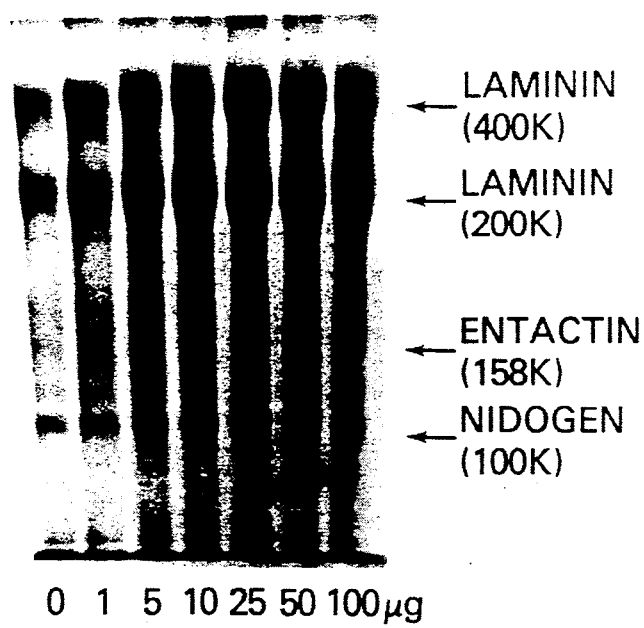
Type IV Collagen Added
FIG. IB
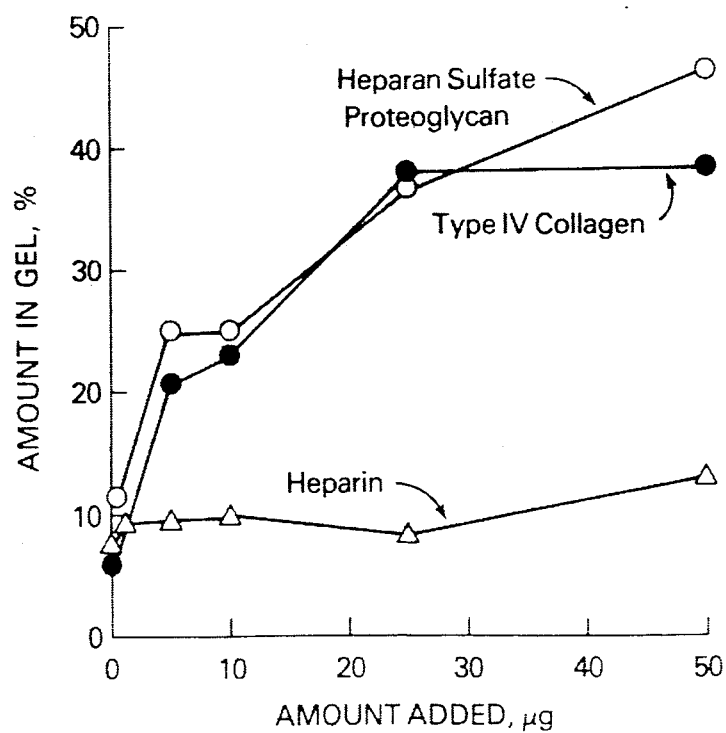

FRACTION NUMBER

FRACTION NUMBER

SDS POLYACRYLAMIDE GEL OF
2.0 M UREA PLACENTA EXTRACT
AFTER HEPARIN AFFINITY
CHROMATOGRAPHY

NO ADDITIONS        HUMAN MATRIGEL

DETERMINING METASTIC POTENTIAL OF TUMOR CELLS AND ISOLATING METASTIC TUMOR CELLS

BACKGROUND OF THE INVENTION

This application is a division of application Ser. No. 06/867,027 filed May 27, 1986, now U.S. Pat. 4,829,06 and is a continuation-in-part of U.S. application No. 06/771,409, filed Aug. 30, 1985, now abandoned.

TECHNICAL FIELD

The present invention relates generally to basement membrane complex. More particularly, the present invention relates to reconstituted, basement-membrane-derived extracellular substratum (matrigel) which polymerizes on heating and promotes cell growth and differentiation in vitro and in vivo.

STATE OF THE ART

Basement membranes are thin, but continuous sheets that separate epithelium from stroma and surround nerves, muscle fibers, smooth muscle cells and fat cells. Basement membranes comprise type IV collagen, the glycoproteins laminin, entactin, nidogen and heparan sulfate proteoglycans. In various studies, these materials show a codistribution within both the lamina densa and its extensions across the lamina lucida. In the electron microscope, the components appear as a network of 5 nm wide cords and their codistribution suggests that the formation of basement membrane occurs through the interaction of various components. Type IV collagen molecules form intermolecular disulfide bonds and associate in a continuous network which can be visualized in basement membranes digested with plasmin (Inoue et al., J. Cell Biol. 97, 1524–1537, 1983).

Various components of the basement membrane are known to interact with each other. In vitro studies with purified components show that laminin binds through its short chains to native but not to denatured type IV collagen and through a domain in its long chain to the heparan sulfate proteoglycan. Each of these basement membrane components is soluble. However, when these macromolecules are mixed together in vitro, they form a floccular precipitate containing laminin to type IV collagen to heparan sulfate proteoglycan in a 1:1:0.1 molar ratio (Kleinman et al, Biochemistry 22, 4969–4974, 1983). However, this precipitate lacks the resiliency and consistency expected of basement membranous structures.

Purified components of basement membrane have been used previously as a coating for cultured cells (Terranova et al., Cell 22:719; 1980). However, such material was soluble and did not form a three dimensional matrix as has been achieved by the composition of the present invention.

SUMMARY OF THE INVENTION

It is, therefore, an object of the present invention to provide a reconstituted, basement-membrane-derived extracellular composition (matrigel) capable of polymerizing on heating and forming a three dimensional matrix which promotes cell growth and differentiation in vitro and in vivo.

It is a further object of the present invention to provide a method of preparing the "matrigel" and promoting cell growth and differentiation therein.

It is a still further object of the present invention to prepare matrigel from human placental extract.

An other object of the present invention is to provide a method of determining metastatic potential of tumor cells and of isolating metastatic tumor cells.

Other objects and advantages of the present invention will become apparent as the detailed description of the invention proceeds.

BRIEF DESCRIPTION OF DRAWINGS

These and other objects, features and many of the attendant advantages of the invention will be better understood upon a reading of the following detailed description when considered in connection with the accompanying drawings wherein:

FIG. 1 shows the effect of type IV collagen, heparan sulfate proteoglycan, and heparin on the gelation of basement membrane components from the basement membrane extract. Increasing amounts of each component were added to 100 μl of the extract and incubated for one hour at 35° in 0.15M NaCl, 0.05M Tris-HCl, pH 7.4. The samples were then centrifuged and insoluble material was dissolved in sample buffer. Equal aliquots of the samples were electrophoresed in 5% acrylamide. Densitometric scans of negatives of photographs of the gels were used to quantitate the amount of protein pelleted. (A) The effect of type IV collagen on the amount of total protein in the gel. (B) The quantitative effects of type IV collagen, heparan sulfate proteoglycan, and heparin on the amount of total protein present in the gel;

DETAILED DESCRIPTION OF THE INVENTION

Figure 2:
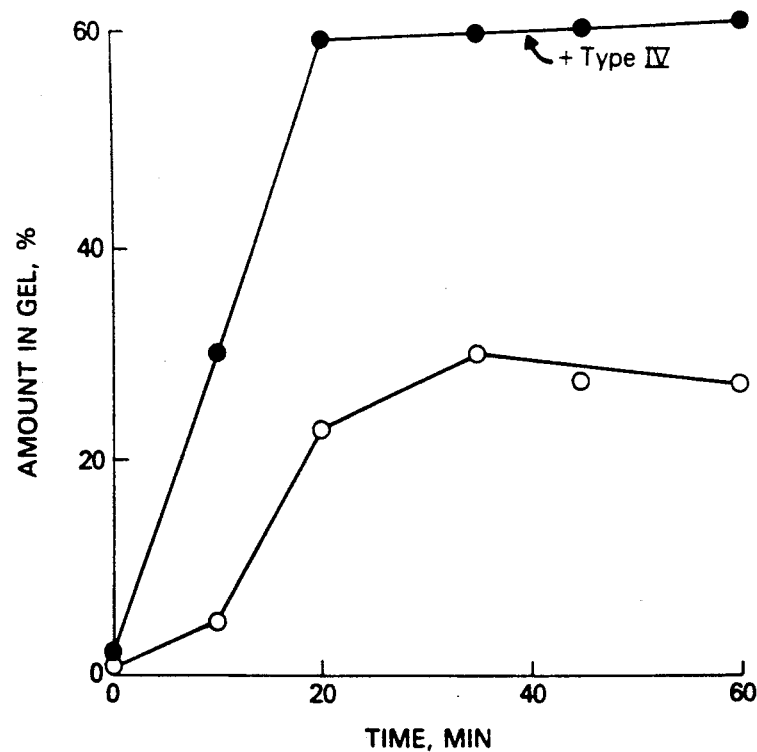
FIG. 2 shows the effect of time and added type IV collagen on the gelation of the basement membrane extract. The conditions are similar to those described in the legend for FIG. 1. This figure compares gelation in the presence (●) and absence (○) of type IV collagen (50 μg)

The above objects and advantages of the present invention are achieved by a basement-membrane-derived composition comprising a biologically active polymerizable extract containing in parts by weight about 60-85% laminin, 5-30% collagen IV, 1-10% nidogen, 1-10% heparan sulfate proteoglycan and 1-5% entactin. The term "biologically active" as used herein means capable of supporting normal growth and differentiation of various cell types when cultured including epithelial cells.

It has been discovered during the studies described herein that under physiological conditions certain components including type IV collagen, laminin, heparan sulfate proteoglycan, nidogen, and entactin interact in rather constant proportions to form a gel with lamellar structures resembling in dimensions those in basement membranes. Under the conditions described herein, each of these components is required for the reconstitution of the matrix. Without being bound to any theory, it is proposed that the components of the gel form supramolecular complexes, which may be intermediates in the formation of the matrix. The gel of the present invention is designated "matrigel" as a descriptive terminology.

The reconstituted matrix (matrigel) promotes the growth and differentation of a variety of cells. In particular, the reconstituted basement membrane gel of the present invention is an excellent substrate for epithelial cells in culture. The matrigel of the present invention has also been demonstrated to promote cell adhesion, growth and differentiation of a multiplicity of cells including neurons, hepatocytes, sertoli cells, hair follicles, thyroid cells and the like. In addition, sertoli cells cultured within the gel have been subsequently transplanted back into the animal with good survival and maturation of the spermatids. The composition of the present invention has also been found to promote nerve regeneration (optic and sciatic) in vivo and allows for organ reconstitution as well. Preparing matrigel using an extract from human placenta also reduces the possibility of immunological interaction or rejection when such matrigel is used in humans.

Although any similar or equivalent methods and materials as described herein can be used for testing or the practice of the present invention, the preferred methods and materials are now described. All publications mentioned hereunder are incorporated herein by reference.

Materials—Type IV collagen, laminin and heparan sulfate proteoglycan were prepared from the EHS (Engelbreth Holm-Swarm) tumor (Timpl et al, J. Biol. Chem. 254:9933–9937; 1979; Hassell et al, Proc. Natl. Acad. Sci. USA 77:4494–4498; 1980; Kleinman, et al, Biochemistry 21:6188–6193; 1982). After washing the tumor tissue in 3.4M NaCl, 0.05 M Tris-HCl, pH 7.4, containing protease inhibitors (Orkin et al, J. Exp. Med. 145:204–220; 1977; Timpl et al, supra), the basement membrane matrix was extracted with 0.5M NaCl in 0.05M Tris-HCl, pH 7.4. Laminin was isolated from the 0.5M NaCl extract as described by Timpl et al, supra. The residue of tumor tissue from lathyritic animals was extracted with 2.0M guanidine in 0.05M Tris-HCl, pH 7.4, followed by an extraction with the same buffer containing 0.005M dithiothreitol to solubilize the type IV collagen (Kleinman et al, supra). Low density heparan sulfate proteoglycan was purified from 6.0M urea extracts of the tumor by ion exchange chromatography followed by cesium chloride density centrifugation and molecular sieve column chromatography (Hassell et al, supra). Heparin was obtained from Sigma Chemical Company.

Unfractionated extracts of the basement membrane matrix were prepared by treating the tissue which had been washed with hihh salt with an equal volume (1 ml/gm) of 2M urea, 0.05 M Tris-HCl, pH 7.4, overnight at 4° and centrifuging at 10,000 g for 30 minutes. The residue was washed once with the same volume of buffer. Then the extract and wash were combined, dialyzed against 0.15M NaCl in 0.05M Tris-HCl, pH 7.4 (TBS), and centrifuged to remove a small amount of insoluble material. The supernatant fraction was stored at −20° C. in small aliquots and used in the reconstitution assays described below. Using established, quantitative ELISA assays, this extract was found to contain laminin (3.5 mg/ml), type IV collagen (0.1 mg/ml) and heparan sulfate proteoglycan (0.1 mg/ml). Entactin, nidogen, and other minor components were also present. For the column chromatography, the extract was dialyzed into 0.5M NaCl, 0.05M Tris-HCl, pH 7.4, and centrifuged to remove insoluble material.

Reconstitution Assays—Gelation was carried out in a centrifuge tube to which 0.05-0.1 ml of the 2M urea extract was added in physiological buffer. Purified components dissolved in 0.15M NaCl, 0.05 Tris-HCl, pH 7.4, were added to the extract or were incubated together at the concentrations indicated. The final volume was made up to 0.5 or 1.0 ml with 0.15M NaCl, 0.05M Tris-HCl, pH 7.4, and the samples were incubated for 1 hour at 35° C. Insoluble material was isolated by centrifugation and the pellets were dissolved in sample buffer and electrophoresed in either 5% or 7.5% acrylamide under reducing conditions (Laemmli, 1970, Nature—London, 227:680-682). Each experiment was repeated a minimum of three times. The total amount of protein in the precipitate was determined by the standard Lowry procedure. The amount of nidogen and entactin in the gel was related to the total amount of material present in the 400K band of laminin by scanning negatives of photographs of the gels in a Helena densitometer (Quick Scan Model, Helena Lab Corp., Beaumont, Tex.). Entactin and nidogen were identified based on their migration in SDS gels and cross reactivity in Western blot analyses with suitable antibodies. Type IV collagen in the gel was quantitated using $^{14}$C-labeled type IV collagen and heparan sulfate proteoglycan was quantitated using $^{35}$S-sulfate labeled material of known specific activities in separate but parallel experiments.

Rotary Shadowing—The 2.0M urea extract equilibrated in 0.5M NaCl, 0.05M Tris-HCl, pH 7.4, was placed on a Sepharose 4B column. An aliquot (30 μl) of the peak fraction (0.1 mg/ml) eluting from the column was diluted with 300 μl of 0.155 M ammonium acetate, pH 7.4, and 600 μl of glycerol. For rotary shadowing, the mixture was sprayed onto mica, shadowed with platinum-palladium, carbon coated, and examined in a JEOL 100C electron microscope.

Ultrastructure of Reconstituted Components—The gel was prepared essentially as described above. Briefly, 0.2 ml of the extract was incubated alone or in the presence of type IV collagen and heparan sulfate proteoglycan overnight at 35° C. The gel was isolated by centrifugation and then fixed in 2.5% glutaraldehyde, treated with 1% OsO$_4$, block stained with 2% uranyl acetate, and dehydrated. The gel was then processed through Epon (Ladd Research Industries, Inc., Burlington, VT; LX-112 resin) for electron microscopy. Thin sections were stained with uranyl acetate and lead citrate, and examined in a JEOL 100° C. electron microscope. Thin sections of rat kidney tubule basement membranes were obtained as described by Laurie et al, (Am. J. Anat. 169:463-481; 1984).

Cell Culture—B16C3 cells were cultured either directly on tissue culture plastic or on a 1 mm thick basement membrane gel in a mixture of F12 medium and DMEM (Dulbecco's modified Eagle's medium, lacking phenol red for visualization of the pigmentation of the cells) containing glutamine, antibiotics, 20 mM tyrosine and 5% fetal calf serum. After one week, the cells were photographed.

The assembly of basement membrane components was analyzed using purified basement membrane components as well as unfractionated extracts of basement membrane. Purified type IV collagen, laminin and heparan sulfate proteoglycan formed a flocculent precipitate when incubated under physiological conditions for one hour at 35°. In contrast, a gel formed when urea extracts of basement membrane are dialyzed against physiological saline and then warmed to 35° for one hour. The components of the gel were isolated by centrifugation and examined by SDS gel electrophoresis. As shown in FIG. 1A, the amount of laminin, entactin, and nidogen present in the gel increased in proportion to the amount of type IV collagen added until 50-60% of the material in the extract was incorporated into the gel. Heparan sulfate proteoglycan also caused increasing amounts of basement membrane components to precipitate (FIG. 1B). Separation by gel electrophoresis and quantitation of the major components in the gel indicated that constant ratios of laminin, entactin, and nidogen are obtained in the presence of added type IV collagen (FIG. 1A) or of heparan sulfate proteoglycan (FIG. 1B). When both type IV collagen (150 μg) and heparan sulfate proteoglycan (10 μg) were added to the extract, up to 80% of the protein in the incubation was incorporated into the gel. The smaller chain of laminin co-electrophoresed with the chains of type IV collagen and prevented its visualization in the SDS gel.

To estimate the amount of type IV collagen in the gel, $^3$H-labeled type IV collagen of known specific activity was used and the amount of $^3$H-label in the precipitate was used as a measure of type IV collagen. Likewise, the heparan sulfate proteoglycan cannot be visualized in the gels and $^{35}$S-labeled heparan sulfate proteoglycan was used. These studies showed that laminin accounted for almost 60% (264±56 ug) of the material in the gel in a typical experiment, whereas type IV collagen was 30% (125±7 μg), heparan sulfate proteoglycan was less than 2% (8±0.7 μg), nidogen was 5%, and entactin was less than 1%. In contrast, supplemenration of the extract with either type I collagen, fibronectin or heparin (FIG. 1b) did not cause any increased precipitation indicating that specific interactions are involved. Removal of the protein core of the proteoglycan by incubation overnight with 0.5N NaOH destroyed its ability to induce polymerization suggesting that the protein portion of the proteoglycan is involved in binding to other components.

Figure 3:
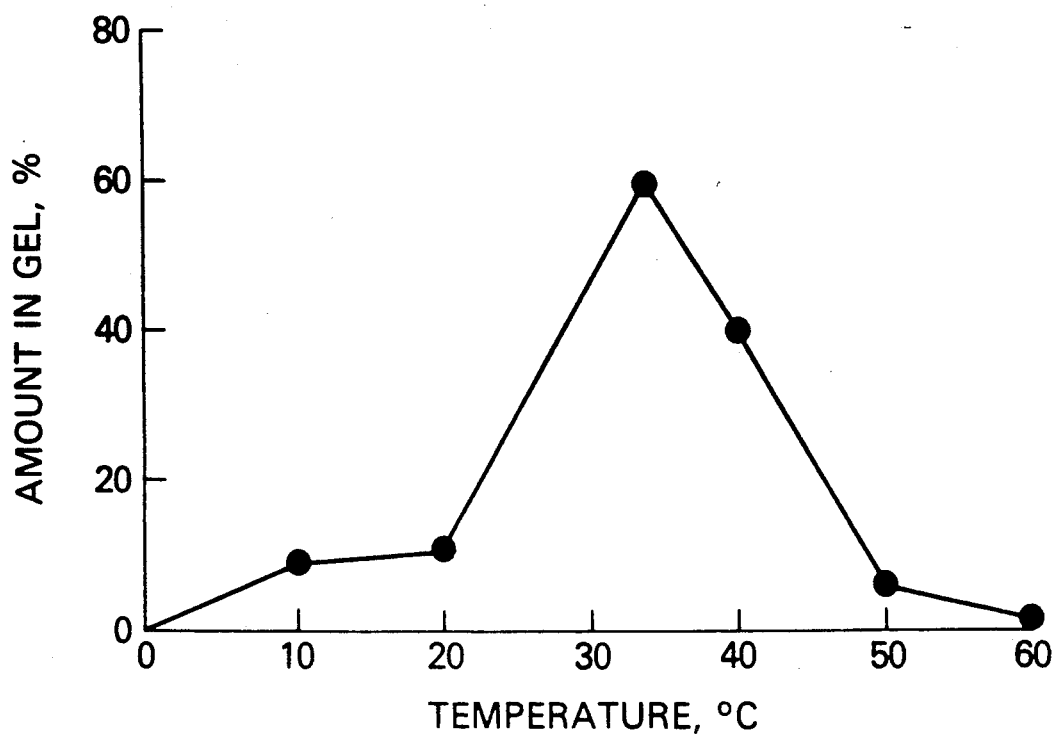
FIG. 3 shows the effect of temperature on the gelation of extracts of basement membrane. The experiment was carried out in the presence of type IV collagen (50 μg) as described in the legend for FIG. 2. Gelation was stopped by centrifugation at the times indicated.

Under physiological conditions, the gelation process is complete within 20 minutes (FIG. 2). The formation of the gel is strongly dependent on temperature with maximum polymerization at 35° C. (FIG. 3). The lack of interaction at 50° C. suggests that thermal denaturation inactivates a critical constituent.

Figure 4:
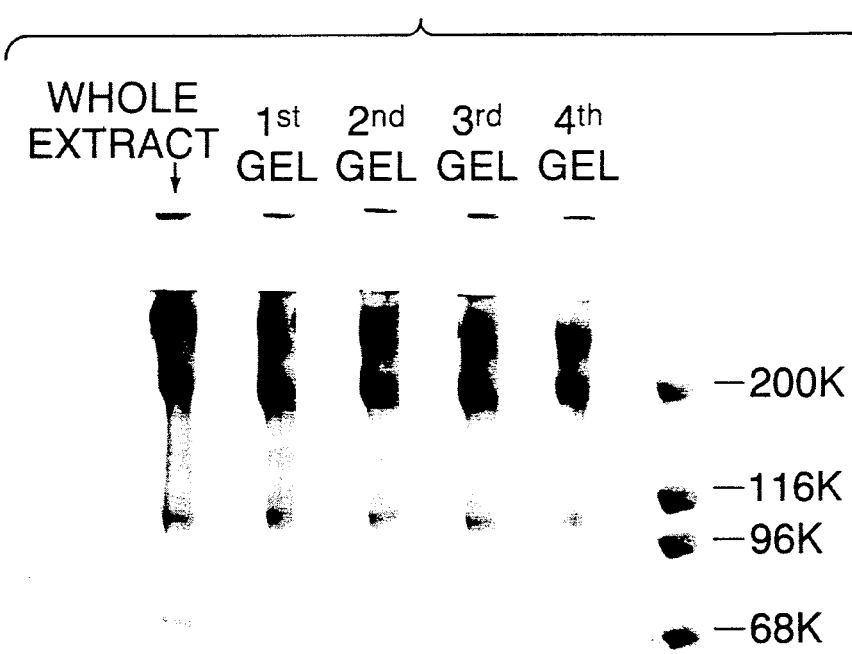
FIG. 4 shows the ability of the basement membrane extract to re-gel following dissolution of the gel. The first lane, designated "whole extract" demonstrates the components in the starting material. The "first gel" designates the components in the gel formed in the presence of type IV collagen. The material present in the gel formed in the absence of type IV collagen (not shown) was solubilized for 20 minutes in 2.0M guanidine, dialyzed against 0.05M Tris-HCl, pH 7.4, containing 0.15M NaCl and allowed to regel in the absence (not shown) and presence of type IV collagen ("designated 2nd gel"). The cycle was repeated two additional times ("3rd" and "4th gels"). Shown are equal aliquots of the gels electrophoresed in a 5% acrylamide gel.

The stability of the gel to dissolution was examined by using various solvents. The gel was not dissolved by cold aqueous salt but was partially dissolved by acidic solutions (Table 1) and completely dissolved in guanidine or in urea solutions. This suggests that the components are linked by relatively strong non-covalent bonds. When the guanidine-dissolved gel was dialyzed against physiological buffers and warmed in the presence of type IV collagen, gel-like structures were reconstituted. This process could be repeated several times with similar proportions of laminin, nidogen, and entactin being deposited at each step as determined by SDS polyacrylamide gels (FIG. 4). In the presence of added type IV collagen, reformation of the gel occurred more rapidly and greater amounts of the components were deposited.

TABLE I

SOLUBILIZATION OF RECONSTITUTED BASEMENT MEMBRANES

| Solvent | % Solubilized |
|---|---|
| 0.15 M NaCl | 0 |
| 0.5 M NaCl | 0 |
| 0.5 M HAc | 43 |
| 1.0 M urea + Dithiothreitol | 40 |
| 2.0 M urea | 73 |
| 2.0 M Guanidine | 97 |

All solutions except the 0.5 M HAc were buffered with 0.05 M Tris-HCl at pH 7.4. The solubilization was carried out at 24° for 20 minutes. After 20 minutes with frequent vortexing, the solutions were centrifuged and the pellets were redissolved and electrophoresed in SDS gels with a reducing agent. The relative amount of material in the pellets was determined by scanning the SDS gels.

Figure 5A:
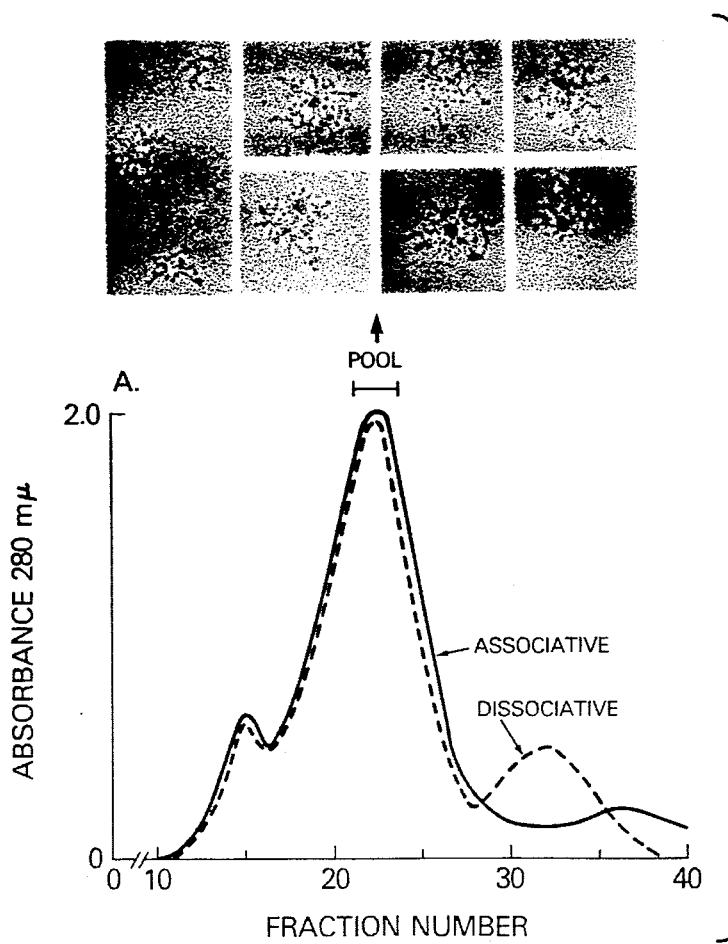
FIG. 5 shows Sepharose 4B column chromatography of the 2.0M urea extract. Two ml of the whole extract equilibrated in either 2M urea, 0.15M NaCl, 0.05M Tris, pH 7.4 (dissociative), or 0.5M NaCl, 0.05M Tris, pH 7.4 (associative), were placed on a Sepharose 4B column (2×60 cm) equilibrated in the corresponding buffer (A). Aliquots of the designated fractions from the extract chromatographed in associative (B) or dissociative (C) conditions were analyzed by SDS polyacrylamide gels. In addition, an aliquot of the material eluting from the column run under associative conditions was examined in the electron microscope by rotary shadowing (A). The electron micrographs show the most common complex in the peak fractions involves a central heparan sulfate proteoglycan and numerous peripheral laminin molecules. Entactin and nidogen are smaller molecules and are not readily visualized in these complexes, but are known to be present.
Figure 5B:
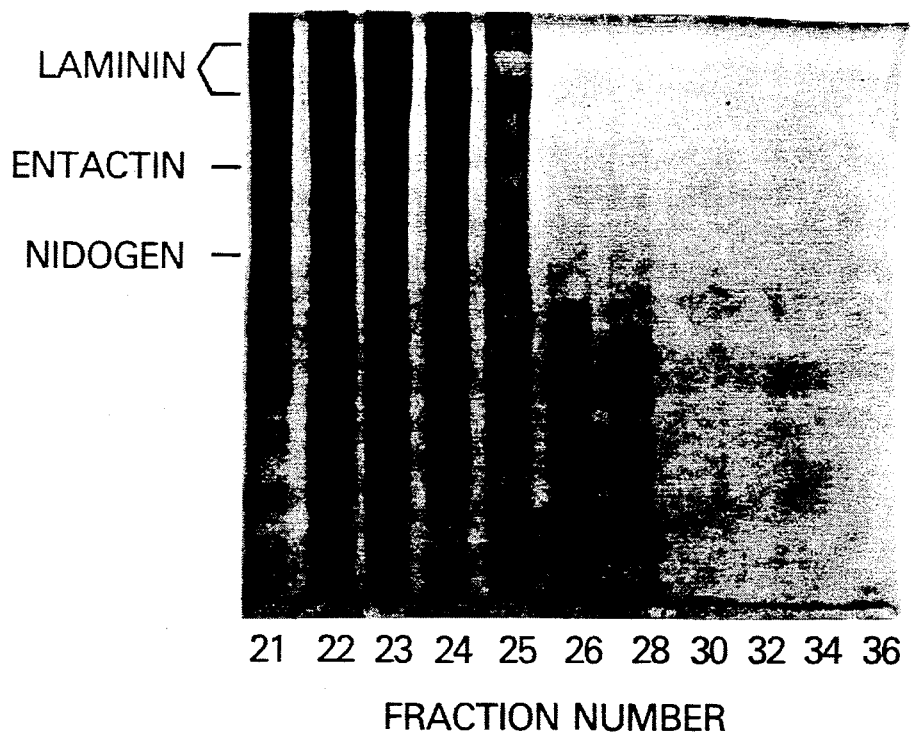
Figure 5C:
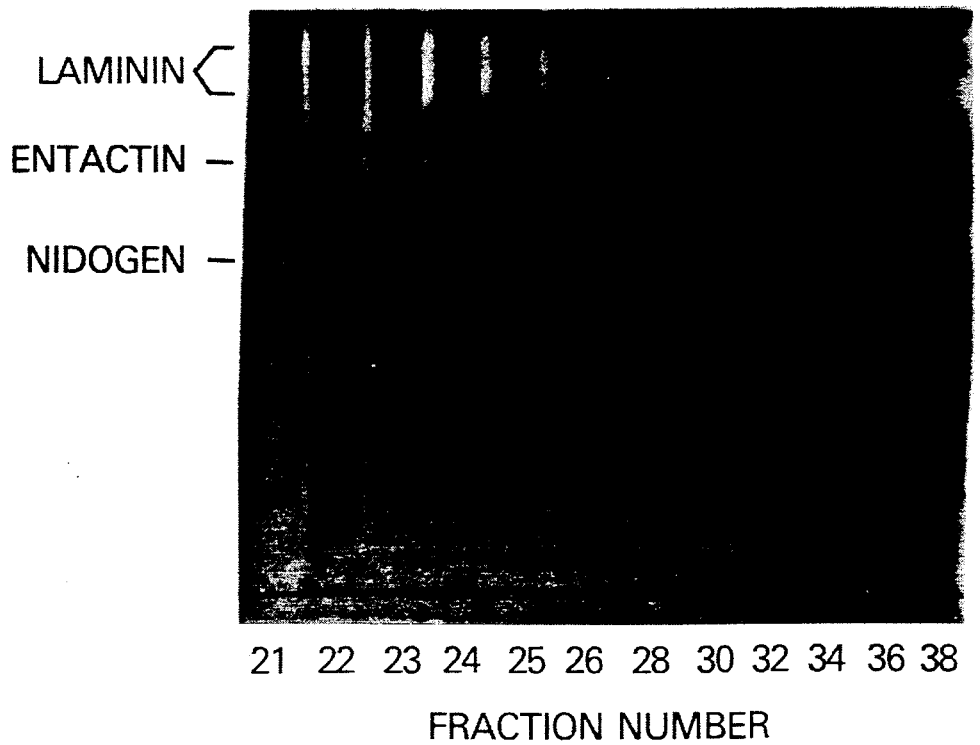

Determination was also made whether soluble complexes of basement components existed. When the urea extract was dialyzed free of urea and passed over a Sepharose 4B column in 0.5M NaCl (associative conditions), laminin, nidogen, and entactin eluted in a major included peak (FIG. 5A & B). When the material in the major included peak was pooled and rerun over the same molecular sieve column in 4M guanidine (dissociative conditions), these components separated in the manner expected from their molecular weights (FIG. 5A & C). These results indicated that there are strong but noncovalent bonds joining laminin, nidogen, and entactin in the complex. Rotary shadowing electron microscopy of the major included peak material confirmed the presence of soluble complexes (FIG. 5A). The complexes involved the large proteoglycan which appears as a large globule due to collapse of the heparan sulfate side chains in this kind of preparation surrounded by several laminin molecules. The nidogen and entactin molecules could not be distinguished but are known to be in the complexes from SDS polyacrylamide gels (FIG. 5B).

Figure 6:
FIG. 6 shows electron micrographs of reconstituted gels and an authentic basement membrane. (A) Gel formed in the absence of added type IV collagen or heparan sulfate proteoglycan. The gel consists of dispersed segments with occasional interconnections. (B) Gel formed in the presence of added type IV collagen and heparan sulfate proteoglycan. The edge of the gel is at the top. The gel consists of an interconnected network; the network is made up of structures which are similar in width to the lamina densa part of native basement membranes. These lamina densa-like structures vary somewhat in thickness. (C) Kidney tubule basement membrane from a 100 gm rat. The basement membrane consists of the lamina lucida and lamina densa. Extensions from the lamina densa attach it to the cell membrane (arrowheads). Bar=200 μm. ×47,500.

The ultrastructure of the reconstituted basement membrane either with or without type IV collagen and heparan sulfate proteoglycan was also examined. In the absence of added type IV collagen and heparan sulfate protecglycan, the gel consisted of numerous widely separated thin, filamentous aggregates (FIG. 6A). The addition of type IV collagen or of heparan sulfate proteoglycan plus type IV collagen (FIG. 6B) resulted in the formation of thin sheets which were interconnected (FIG. 6B) or were confluent. The individual segments of the network had an average width similar to that of the lamina densa of kidney tubule basement membrane (FIG. 6C). However, unlike native basement membranes in which lamina densa-like layers are arranged in parallel, such as for example the PYS tumor basement membranes (Martinez-Hernandez et al, Lab Invest. 47:247-257, 1982) or Reichert's membrane (Inoue et al, J. Cell. Biol. 97:1524-1537, 1983), the lamina densa-like structures were interconnected and did not form parallel multilamellar structures. At very high power in the electron microscope, each segment could be resolved into 5 nm cords as previously described in other basement membranes (Inoue et al, supra, Laurie et al, J. Cell. Biol. 99, 78a; 1984).

Figure 7A:
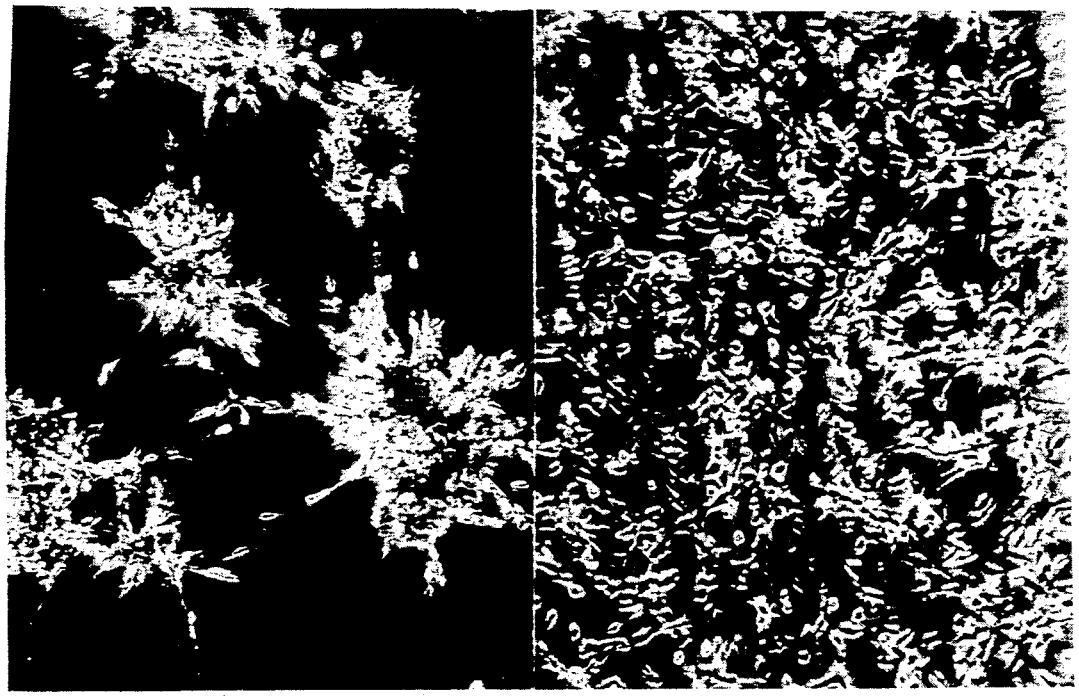
FIG. 7 shows the effect of the basement membrane gel on the morphology and differentiation of B16C3 melanoma cells in culture. Sterile 2M urea extract of the EHS-tumors in 0.15M NaCl, 0.05M Tris-HCl, pH 7.4, was allowed to gel on the surface of a petri dish for 30 minutes at 37°. Then equal numbers of cells were plated onto the gel (left) or onto control tissue culture plastic dishes (right). After one week in culture in DMEM containing 20 mM tyrosine, gentamicin, glutamine and 5% fetal calf serum, the cells were photographed. (A) Morphology and assessment of melanogenesis by the cells. (B) Direct view of the dishes. The gel at the edge has been deflected to show that the cells are attached to it.
Figure 7B:
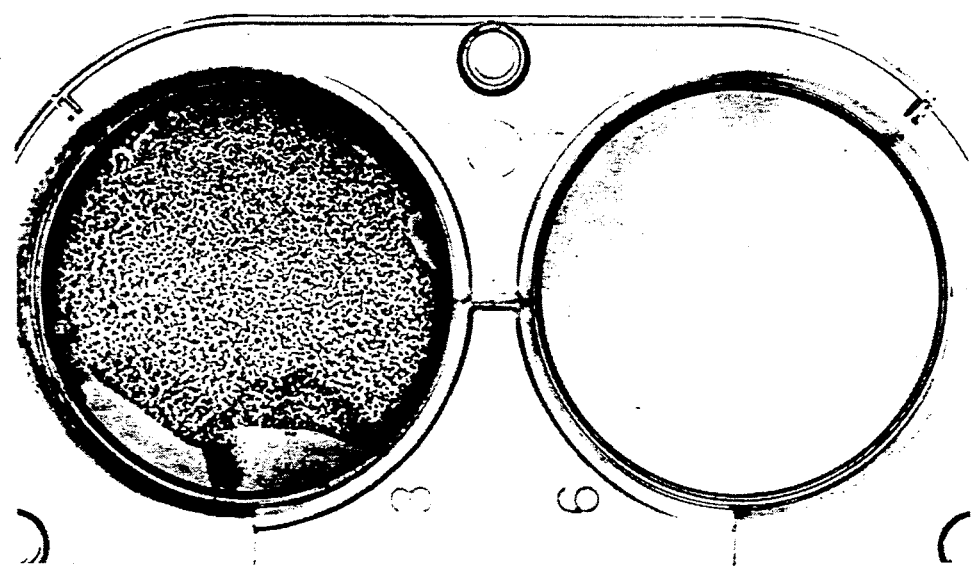

The matrigel (reconstituted basement membrane) was used to coat the surfaces of bacteriological petri dishes and tested as a substrate for the growth and differentiation of a variety of cells at different laboratories. Melanoma cells (B16C3) showed considerable differences in morphology when grown on the basement membrane gel as compared to tissue culture surfaces (FIG. 7). Further, there was a much earlier and more extensive pigmentation of the cells on this substrate. Studies of other cells showed that endothelial cells formed tube-like structures on the gel and that hepatocytes survived longer on basement membrane gel substrates than on tissue culture plates or on type I collagen. In vivo, the basement membrane gel was found to promote peripheral nerve regeneration (Madison et al, 1985. Exptl. Neurol., 88:767-772).

Such studies indicate that the reconstituted basement membrane is a biologically active substrate which induces diverse cellular responses. Since it can support cell adhesion, growth and differentiation beyond that known for the individual components, without being bound to any theory it is postulated that the reconstituted basement membrane gel contains these molecules in a unique and active conformation.

EXAMPLE 1

Preparation of EHS Tumor Extract for Gelation and Cell Culture

The procedure is based on about 100 g of tumor and all steps are carried out at 4° C. unless indicated otherwise.

1. Homogenize tumor in 200 ml of 3.4 NaCl buffer comprising
3.4M NaCl (397 g)
0.05M Tris (12.1 g)
0.004M EDTA (3.0 g)
0.002M NEM (0.5 g).
Add H$_2$O to 2 Liters,
adjust pH to 7.4.
2. Centrifuge at 10,000 RPM for 15 minutes, discard supernatant.
3. Homogenize tumor residue in 3.4M NaCl buffer.
4. Centrifuge at 10,000 RPM for 15 minutes, discard supernatant.
5. Homogenize tumor residue in 3.4M NaCl buffer.
6. Centrifuge at 10,000 RPM for 15 minutes, discard supernatant.
7. Homogenize tumor in 100 ml of 2M urea buffer comprising
2M urea (240 g)
0.05M Tris 12.1 g)
0.15M NaCl (18 g).
Add H$_2$O to 2 liters and
adjust pH to 7.4.
8. Stir overnight at 4° C.
9. Centrifuge at 14,000 RPM for 20 minutes. Save supernatant.
10. Add 50 ml of 2M urea buffer to the tumor residue and homogenize.
11. Centrifuge at 14,000 RPM for 20 minutes. Save supernatants.
12. Combine supernatants and dialyze vs Tris-saline comprising
0.05M Tris (12.1 g)
0.15M NaCl (18.0 g)
Add H$_2$O to 2 liters.
adjust pH to 7.4.

Use a graduated cylinder for 1 liter. Add 900 ml of Tris-saline +5ml of chloroform (this is a sterilization step).
13. Dialyze 2 hours—rotate bags at end.
14. Change dialyses to Tris-saline alone.
15. Dialyze one more change with Tris-saline.
16. Last dialysis steps should be against media salts such as DMEM or Dulbecco-Vogt or the like.

17. Inside of bag is sterile. Render the outside of the bag sterile with alcohol, rinse hemostat and scissors in alcohol and empty bags in sterile hood into sterile containers. Aliquot as needed. Collagen IV can be optionally added at this stage to the liquid phase in an amount ranging from about 0.1 to 1 mg/ml depending on the desired consistency or strength of the polymerized gel matrix. The thicker gels have been found to be more durable.

18. Immediately cool. Cryopreserve at $-20°$ C. if storage is desired. For gelation: pour extract into desired containers and warm (about 2420 -35° C.) for 30-120 minutes for polymerization. For a 35 mm petri dish, use less than 1 ml of the extract. Spread it thin.

19. To use the gel as a cell culture substratum, add about 3 ml of suitable growth medium on top of the polymerized gel obtained from step 18 and inoculate the medium with the dispersions of the cells which are desired to be grown. Of course, the growth medium to be used will depend on the type of the cell which is desired to be grown; specific standard growth medium and conditions (e.g. $CO_2$ concentration, temperature, pH and the like) for different types of cells being well known in the art.

An alternate procedure for promoting the growth of some cell types is to inoculate or disperse the cells in the cold liquid extract just before polymerization in step 18 and then proceed with polymerization and subsequent steps the same as described in step 19. For example, hair follicle, sertoli cells and the like are apt to be better cultured if first dispersed in the liquid phase prior to polymerization whereas epithelial cells, exocrine acinar cells, sciatic nerve cell, spinal cord neuron, thyroid organ culture, and the like are better cultured on top of the polymerized gel.

EXAMPLE 2

Human Placental Preparation of Basement Membrane Matrigel

Extracts comparable in composition and in biological activity can also be obtained from human placenta using a process similar to that used for the EHS mouse tumor described herein. However, since placenta is not composed of pure basement membrane like the EHS mouse tumor, an additional step is necessary as described hereunder:

(a) Placenta is freed of cord and amnion.

(b) Placenta is then washed and homogenized in about 3.4 M NaCl in 0.05 M Tris-HCl, pH 7.4 containing standard protease inhibitors such as phenylmethyl sulfonyl fluoride; n-ethylmaleimide EDTA, pepstatin and the like.

(c) The tissue residue is extracted overnight at about 4° C. with an equal volume (g/ml) of 0.5 M NaCl in 0.05 M Tris-HCl, pH 7.4.

(d) The tissue after buffer extraction is washed with an equal volume of the same buffer and combined with the extract.

(e) The tissue residue is extracted overnight at about 4° C. with an equal volume (g/ml) of 2.0 M urea in 0.05 M Tris-HCl, pH 7.4.

(f) Both the 0.5 M NaCl extract and the 2.0 M urea extract are dialyzed against 0.02 M sodium phosphate buffer, pH 7.4 overnight at 4° C. and the dialyzed samples are separately chromatographed on a heparin Sepharose column equilibrated in 0.02 M sodium phosphate buffer, pH 7.4, containing 0.15 M NaCl. The bound material is eluted with 1.0 M NaCl and dialyzed into Eagle's minimal essential medium.

Characterization and Biological Activity of Placenta Extract

Figure 8:
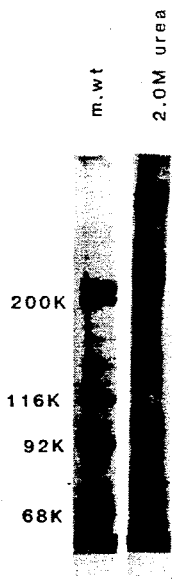
FIG. 8 is Coomassie blue stain of 2.0 M urea extract of placenta after heparin affinity chromatography showing the purification of laminin.

The placental extract before and after heparin sepharose chromatography were compared for the purity of the extract. To do so, the 0.5 M NaCl and 2.0 M urea extracts and the bound materials from the heparin column were dialyzed against water, lyophillized, and electrophoresed in SDS polyacrylamide gels. The samples were then stained with Coomassie blue for a profile on the protein content and immunoreacted with anti-laminin antibodies after transfer to nitrocellulose. These results demonstrated that laminin, the major component of basement membranes, as of the mouse basement membrane preparation described herein, is present in the placenta extracts in intact form as clearly demonstrated after heparin affinity chromatography (FIG. 8). Placental laminin contains chains of $Mr=400,000$ and $Mr=200,000$ components.

Figure 9:
FIG. 9 shows the effect of human placental matrigel on neuronal process formation. The results show that the human matrigel strongly promotes neurite outgrowth.

The biological activity of this material on neurite outgrowth was tested using NG108-15 neuroblastoma plus glioma hybrid cells in culture. These cells respond rapidly (within 2 hours) to the extracts as well as to the heparin bound material by sending out long neuritic processes (FIG. 9). The material to be tested is added in Eagle's minimal essential medium lacking serum or some other culture medium along with freshly dissociated cells. After two hours on tissue culture plastic, extended processes are observed in the cells exposed to the placental material. Thus, the placenta materials have comparable activity to the murine tumor material in stimulating neurite process development.

Use of Basement Membrane Material From Murine Tumor to Assay For Tumor Cell Invasiveness and To Select For Invasive Tumor Cells In order for all tumor cells to metastasize, they must enter the blood stream and then exit from it to grow at a distant site. Tumor cells must therefore adhere to, degrade, and migrate through endothelial basement membranes in order to metastasize. These steps are critical in tumor cell metastasis. A unique in vitro assay to measure these critical steps in the invasion process has now been devised. The assay is fast, quantitative, reproducible, and distinguishes between nonmetastatic and metastatic cells. This assay employs the murine reconstituted basement membrane described herein.

Assay for Tumor Cell Invasiveness

Figure 10:
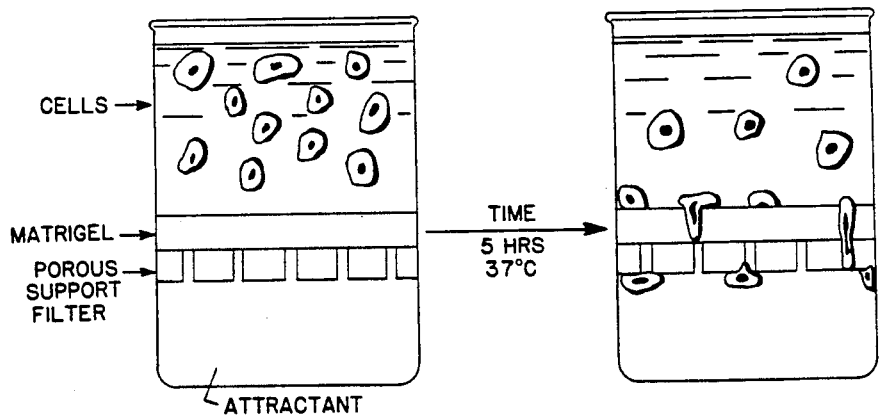
FIG. 10 is a diagramatic representation of Tumor Cell Invasiveness Assay using matrigel.

A porous filter (Nucleopore) is placed inside a blind well Boyden chamber. The lower compartment contains an attractant such as fibroblast conditioned medium or laminin. Fifty microliters of murine basement membrane extract are placed on top of the filter in the upper compartment and allowed to polymerize at 37° C. Then cells in Eagle's minimal essential medium or some other suitable culture medium are added to the upper well and the entire chamber is incubated at 37° C. in 95% air, 5% $CO_2$ for 5 hours. During this time, the invasive cells adhere to the matrix, degrade the matrix, and migrate through the matrix and the porous holes in the filter. This process is diagrammatically shown in FIG. 10. The number of cells which have invaded the matrix can be quantitated on the lower side of the filter, for example by direct counting in a microscope after the cells have been stained with DifQuick (Harelco). Alternatively, if the cells are radiolabeled, they can be measured directly in a scintillation counter.

It was observed that cells which are known to be non-metastatic, in vivo, do not invade the matrix, i.e., less than 5 cells per field are observed on the lower surface of the filter. Whereas, cells which are known to be metastatic in vivo invade the matrix, i.e., greater than 10 cells per high power field are observed on the lower surface of the filter. More than 10 murine and human tumor cell lines of known metastatic potential have been tested and it was found that there is a direct relationship between the ability of the cells to adhere to, degrade, and migrate through the reconstituted murine basement membrane and their metastatic potential (Table II).

TABLE II

Tumorgenicity and Invasiveness of Human and Murine Cell LInes

| | Tumor Formation In Vivo | Invasiveness In Vitro |
|---|---|---|
| 10T½ fibroblasts | No | No |
| NIH 3T3 fibroblasts | No | No |
| NIH 3T3 transfected with RAS | Yes | Yes |
| NIH 3T3 transfected with MOS | Yes | Yes |
| NIH 3T3 transfected with SSV | Yes | Yes |
| NIH 3T3 transfected with MMSV | Yes | Yes |
| B16 F1 melanoma | Yes | Yes |
| B16 F10 melanoma | Yes | Yes |
| B16 BL6 melanoma | Yes | Yes |
| B16 Br2 melanoma | Yes | Yes |
| K-1735 melanoma Cl 10 | No | No |
| K-1735 melanoma Cl 10 | Yes | Yes |
| MC-180 epidermoid carcinoma | Yes | Yes |
| A-204 Rhabdomyosarcoma | Yes | Yes |
| PA-1 Teratocarcinoma | Yes | Yes |
| PC-3 prostate carcinoma | Yes | Yes |
| MALME 3 m Melamona | Yes | Yes |
| SW 620 Colon Adenocarcinoma | Yes | Yes |
| MCF-f breast carcinoma | No | No |
| MCF-f breast carcinoma & estradiol | Yes | Yes |
| MCF-f breast carcinoma & ras | Yes | Yes |

Cells were assayed for 5 hours in the Boyden Chamber assay described above. Cell lines which had less than 5 cells/field on the lower surface of the filter were considered non invasive (No), whereas cell lines with 10 cells or more/field on the lower surface were considered invasive (Yes). The ability of the cells lines to form tumors in vivo is available in published literature.

Invasive (Metastatic) Cell Selection

Figure 11:
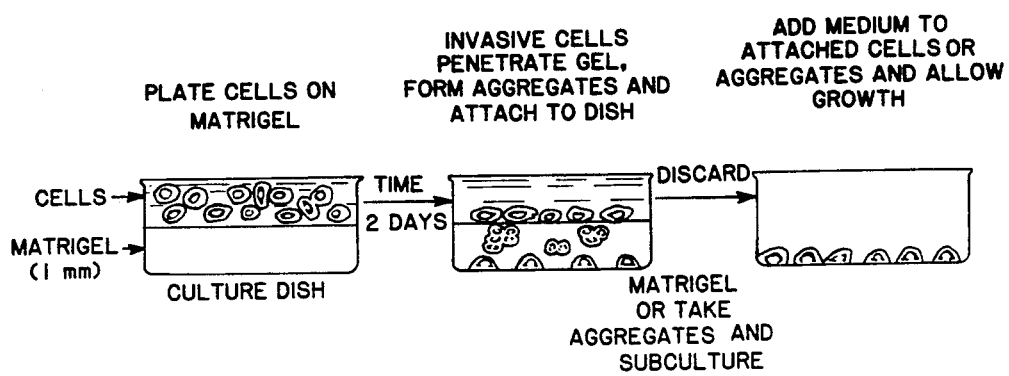
FIG. 11 is a diagramatic representation of Invasive (Metastatic) Cell Selection using matrigel.

Highly invasive tumor cells can also be selected for and obtained in pure form based on their ability to adhere, degrade, and migrate through the reconstituted basement membrane. Here the murine basement membrane extract is placed on a tissue culture dish (0.5 ml/35 mm diameter dish) and allowed to polymerize for 30 minutes at 37° C. The cells are plated in a sterile manner in complete culture medium as required for the growth of the specific cells. After two days, the invasive cells attach to, degrade, and migrate through the matrix to the surface of the plastic dish where they are concentrated. This is shown in FIG. 11. The invasive cells on the plastic surface can be recovered after removal of the reconstituted basement membrane gel.

It was found that non-metastatic cells are unable to complete this process and very few, if any, cells are observed in the Matrigel or on the plastic dish after 2 days (Table III). Metastatic cells are able to adhere to, degrade, and migrate through the matrix to the surface of the culture dish in quantity. When the "selected" cells, i.e., those which have migrated through the matrix, are retested in the Tumor Cell Invasion Assay, a more homogeneous and invasive population of cells is observed.

TABLE III

Number of Cell Aggregates Invading Matrigel Before and After Selection in Matrigel

| Cells | # of aggregates |
|---|---|
| Unselected cells | |
| Cl 10 (non metastatic) | 2 ± 1 |
| Cl 3 (low metastatic) | 6 + 1 |
| M2 (high metastatic) | 16 ± 1 |
| Selected cells | |
| Cl 10 | 19 ± 1 |
| M2 | 19 ± 3 |

All cells were obtained from M. D. Anderson Hospital, Houston TX. The selected cells are the parent lines. The selected cells are those from the parent line which have chemoinvaded the matrigel, been isolated and grown. Upon retesting their ability to invade the matrigel, they are much more invasive. Data are expressed as number of cell aggregates which have invaded the matrigel ±1 S.D.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A method of determining metastic potential of tumor cells, comprising the steps of:
   (a) layering on a suspended nucleopore filter about 50 μl to 100 μl of a tumor cell culture composition comprising an extract containing in parts by weight about 60–85% laminin, 5–30% collagen IV, 1–10% nidogen, 1–10% heparan sulfate proteoglycan and 1–5% entactin, said composition being capable of polymerizing on heating and promoting neurite and epithelial cell growth and differentiation, and allowing the extract to polymerize;
   (b) placing a single cell layer of suspended tumor cells to be tested in a buffered medium on said polymerized layer and allowing said cells to attach and migrate through said polymerized extract at about 37° C. for about 5 hours; and
   (c) then determining the presence of migrated cells of the opposite surface of the nucleopore filter.

2. A method of isolating metastic tumor cells, comprising the steps of:
   (a) layering on a tissue culture dish 1 to 2 ml of a tumor cell culture composition containing an extract containing in parts by weight about 60–85% laminin, 5–30% collagen IV, 1–10% nidogen, 1–10% heparan sulfate proteoglycan and 1–5% entactin; said composition polymerizing on heating and promoting neurite and epithelial cell growth and differentation, and allowing the extract to polymerize;
   (b) placing a single cell layer of suspended tumor cells in a buffered medium on said polymerized layer;
   (c) incubating the culture dish for about 48 hours at about 37° C.;
   (d) removing polymerized matrix from said culture dish; and (e) than allowing cells adhering to the culture dish to grow in a growth medium.

3. A method of determining metastatic potential of tumor cells comprising
(a) layering on a filter a composition comprising, in parts by weight, about 60-85% laminin, 5-30% collagen IV, 1-10% nidogen, 1-10% heparan sulfate proteoglycan and 1-5% entactin, said composition being capable of polymerizing and promoting neurite and epithelial cell growth and differentiation;
(b) subjecting said composition to conditions under which polymerization can be effected, whereby a polymerized layer is formed;
(c) placing a layer of suspended tumor cells to be tested on a first side of said polymerized layer and incubating said tumor cells and said layer under conditions such that migration of metastatic cells present in said suspension through said polymerized layer can be effected; and
(d) determining the presence or absence of migrated metastatic cells on a second side of said layer.

4. A method of isolating metastatic tumor cells comprising
(a) layering on a solid support a composition comprising in parts by weight, about 60-85% laminin, 5-30% collagen IV, 1-10% nidogen, 1-10% heparan sulfate proteoglycan and 1-5% entactin, said composition being capable of polymerizing and promoting neurite and epithelial cell growth and differentiation;
(b) subjecting said composition to conditions under which polymerization can be effected, whereby a polymerized layer is formed;
(c) placing a suspension of tumor cells containing metastatic cells in contact with said polymerized layer and incubating said cells and said layer under conditions such that migration of said metastatic cells present in said suspension through said polymerized layer and adherence of said migrated metastic cells to said solid support can be effected; and
(d) removing said polymerized layer from said solid support under conditions such that said migrated metastatic cells remain adhered to said solid support.

* * * * *